(12) United States Patent
Di Carlo et al.

(10) Patent No.: US 10,688,453 B2
(45) Date of Patent: Jun. 23, 2020

(54) SYSTEM AND METHOD FOR DROPLET FORMATION AND MANIPULATION USING FERROFLUIDS

(71) Applicant: THE REGENTS OF THE UNIVERSITY OF CALIFORNIA, Oakland, CA (US)

(72) Inventors: Dino Di Carlo, Los Angeles, CA (US); Soroush Kahkeshani, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 160 days.

(21) Appl. No.: 15/767,979

(22) PCT Filed: Oct. 7, 2016

(86) PCT No.: PCT/US2016/056148
§ 371 (c)(1),
(2) Date: Apr. 12, 2018

(87) PCT Pub. No.: WO2017/066102
PCT Pub. Date: Apr. 20, 2017

(65) Prior Publication Data
US 2018/0296992 A1   Oct. 18, 2018

Related U.S. Application Data

(60) Provisional application No. 62/241,917, filed on Oct. 15, 2015.

(51) Int. Cl.
*B01F 13/00* (2006.01)
*A61K 9/00* (2006.01)
(Continued)

(52) U.S. Cl.
CPC .......... *B01F 3/0815* (2013.01); *A61K 9/0024* (2013.01); *A61K 9/0097* (2013.01);
(Continued)

(58) Field of Classification Search
CPC .. A61K 9/0009; A61K 9/0021; A61K 9/0024; A61K 9/0097; A61M 2037/0023;
(Continued)

(56) References Cited

FOREIGN PATENT DOCUMENTS

WO      2009/029229 A2    3/2009
WO   WO-2009029229 A2 *   3/2009   .......... B01F 13/0062

OTHER PUBLICATIONS

Yan, Qifan et al., "Magnetically controllable generation of ferrofluid droplets", Microfluidic Nanofluid (2015) 19:1377-1384 (Year: 2015).*
(Continued)

*Primary Examiner* — Jennifer Wecker
(74) *Attorney, Agent, or Firm* — Vista IP Law Group LLP

(57) ABSTRACT

A microfluidic device for forming droplets includes at least one ferrofluid reservoir disposed in the microfluidic device and containing a ferrofluid therein. The microfluidic device includes a continuous-phase reservoir disposed in the microfluidic device and containing an oil phase therein and one or more microfluidic channels connecting between the at least one ferrofluid reservoir and the continuous-phase reservoir, the continuous-phase reservoir comprising a step region having an increased height as compared to a height of the one or more microfluidic channels. To form droplets an externally applied magnetic field is applied to the device to pull the ferrofluid into the continuous-phase reservoir, whereby droplets are formed at step region.

20 Claims, 10 Drawing Sheets

(51) Int. Cl.
*B01F 3/08* (2006.01)
*G01N 35/10* (2006.01)
*B01L 3/00* (2006.01)
*A61M 37/00* (2006.01)

(52) U.S. Cl.
CPC ...... *B01F 13/0059* (2013.01); *B01F 13/0077* (2013.01); *B01L 3/502784* (2013.01); *G01N 35/1002* (2013.01); *A61K 9/0009* (2013.01); *A61K 9/0021* (2013.01); *A61M 2037/0023* (2013.01); *B01L 3/502761* (2013.01); *B01L 2200/0668* (2013.01); *B01L 2300/0816* (2013.01); *B01L 2300/0867* (2013.01); *B01L 2400/043* (2013.01); *G01N 2035/1034* (2013.01)

(58) Field of Classification Search
CPC ............ B01F 13/0059; B01F 13/0077; B01F 3/0815; B01L 2200/0668; B01L 2300/0816; B01L 2300/0867; B01L 2400/043; B01L 3/502761; B01L 3/502784; G01N 2035/1034; G01N 35/1002
See application file for complete search history.

(56) References Cited

OTHER PUBLICATIONS

PCT International Preliminary Report on Patentability (Chapter I of the Patent Cooperation Treaty) for PCT/US2016/056148, Applicant: The Regents of the University of California, Form PCT/IB/326 and 373, dated Apr. 26, 2018 (9pages).
Katsikis, Georgios et al., Synchronous universal droplet logic and control, Nature Physics, 11, 588-596 (2015).
Kahkeshani, Soroush et al., Drop formation using ferrolluids driven magnetically in a step emulsification device, Lab Chip, 2016, 16, 2474-2480.
Kim, Jitae et al., Dual-mode on-demand droplet routing in multiple microchannels using a magnetic fluid as carrier phase, Biomicrofluidics 8, 054105 (2014).
Liu, Jing et al., Numerical study of the formation process of ferrofluid droplets, Physics of Fluids, 23, 072008 (2011).
Liu, Jing et al., Liu et al., Numerical and experimental investigations of the formation process of ferrofluid droplets, Microfluid Nanofluid, 11, 177-187 (2011).
Nguyen, Nam-Trung et al., Magnetowetting and Sliding Motion of a Sessile Ferrofluid Droplet in the Presence of a Permanent Magnet, Langmuir 2010, 26(15), 12553-12559.
Pamme, Nicole, Magnetism and microfluidics, Lab Chip, 6, 24-38 (2006).
Tan, Say-Hwa et al., Formation and manipulation of ferrofluid droplets at a microfluidic T-junction, J. Micromech. Microeng. 20, 045004, (2010).
Yan, Qifan et al., Magnetically controllable generation of ferrofluid droplets, Microfluidic Nanofluid (2015) 19:1377-1384.
PCT International Search Report for PCT/US2016/056148, Applicant: The Regents of the University of California, Form PCT/ISA/210 and 220, dated Jan. 11, 2017 (6pages).
PCT Written Opinion of the International Search Authority for PCT/US2016/056148, Applicant: The Regents of the University of California, Form PCT/ISA/237, dated Jan. 11, 2017 (7pages).

* cited by examiner

FIG. 1A
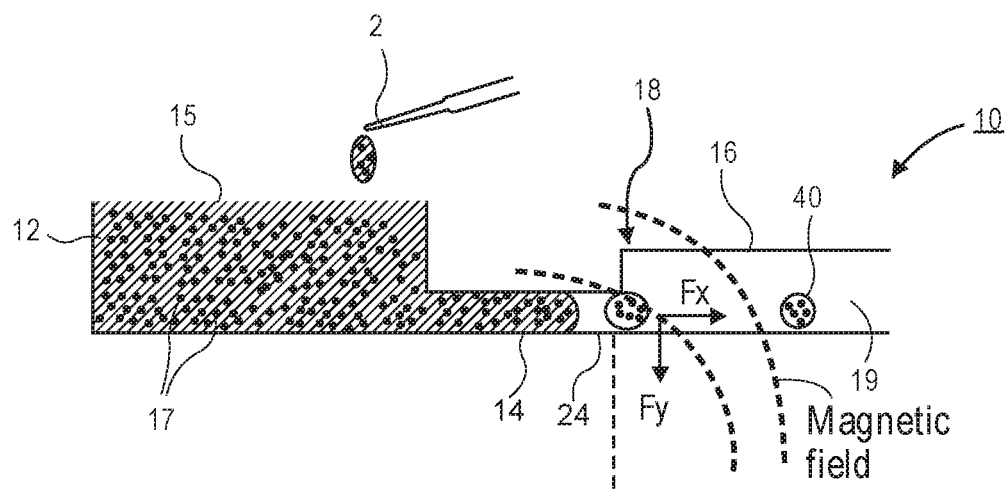
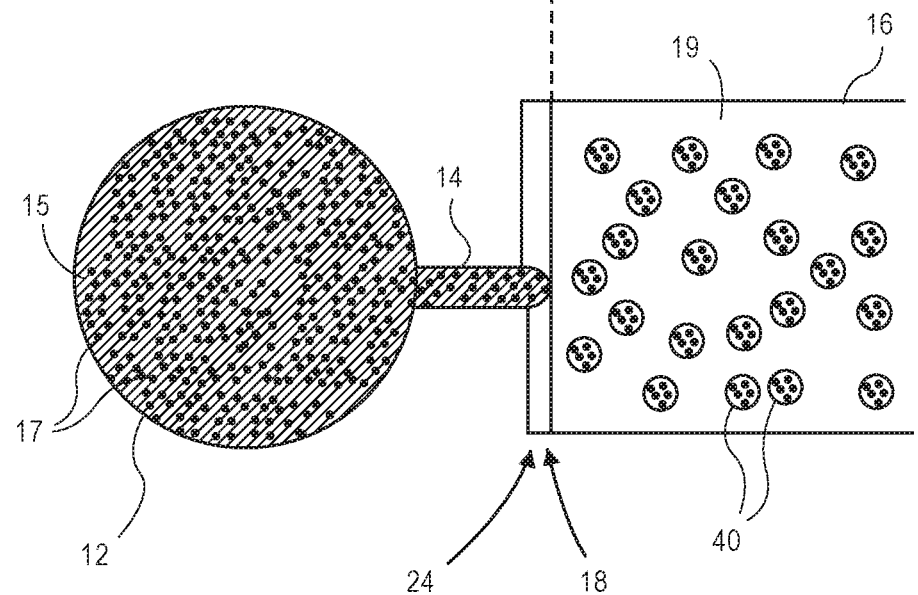
FIG. 1B

FIG. 1C
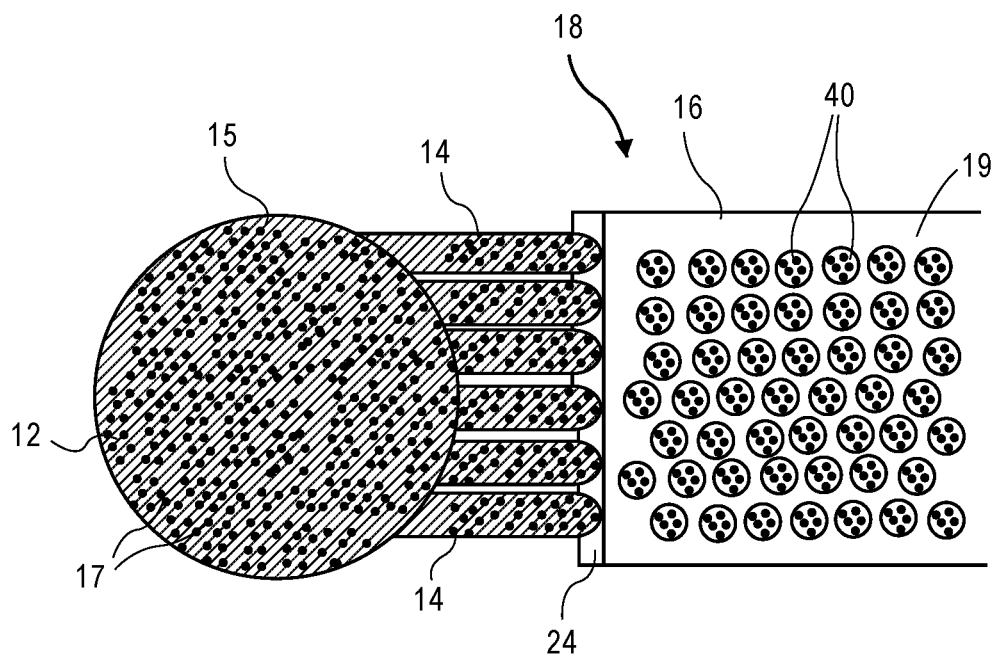
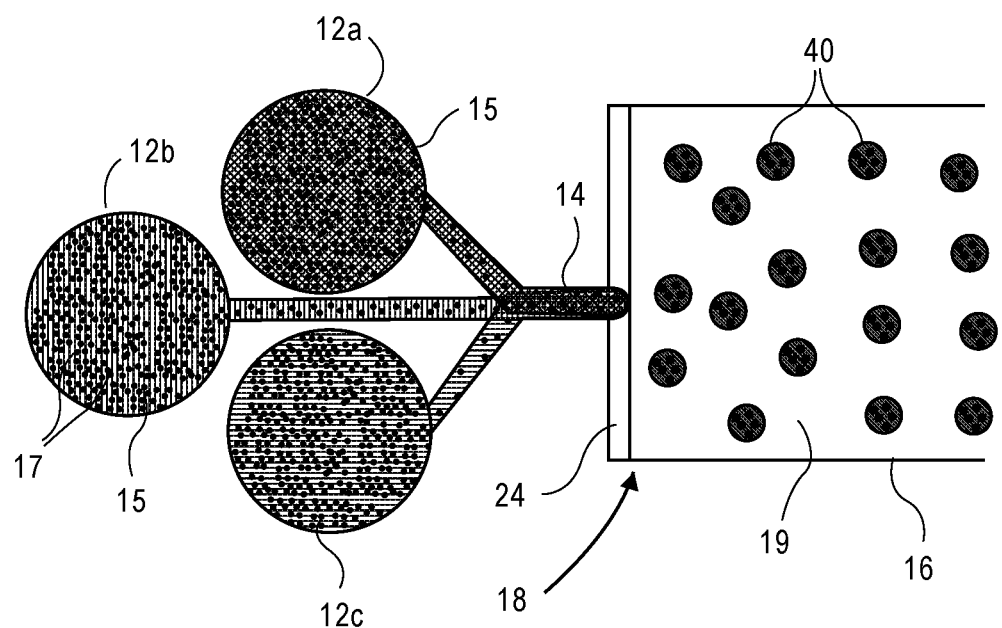
FIG. 1D

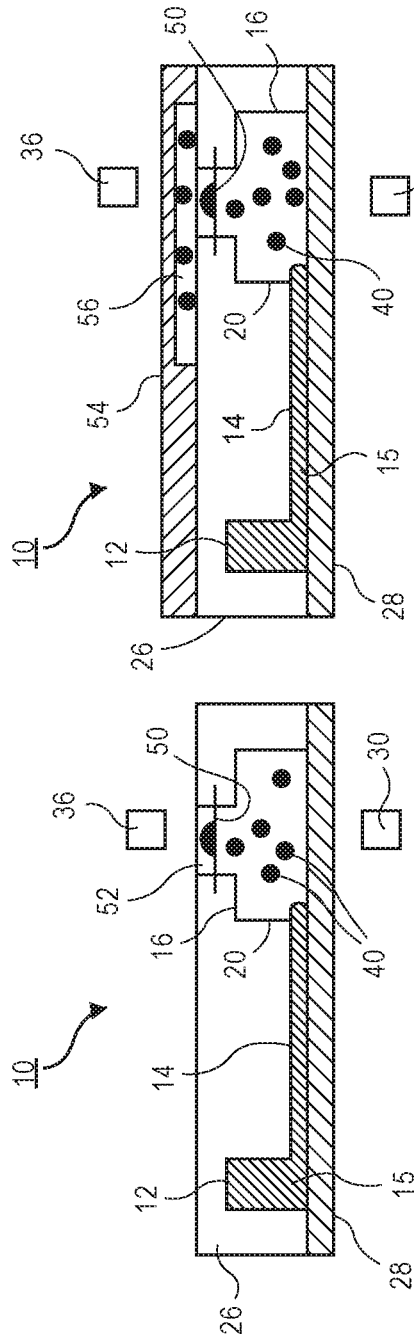
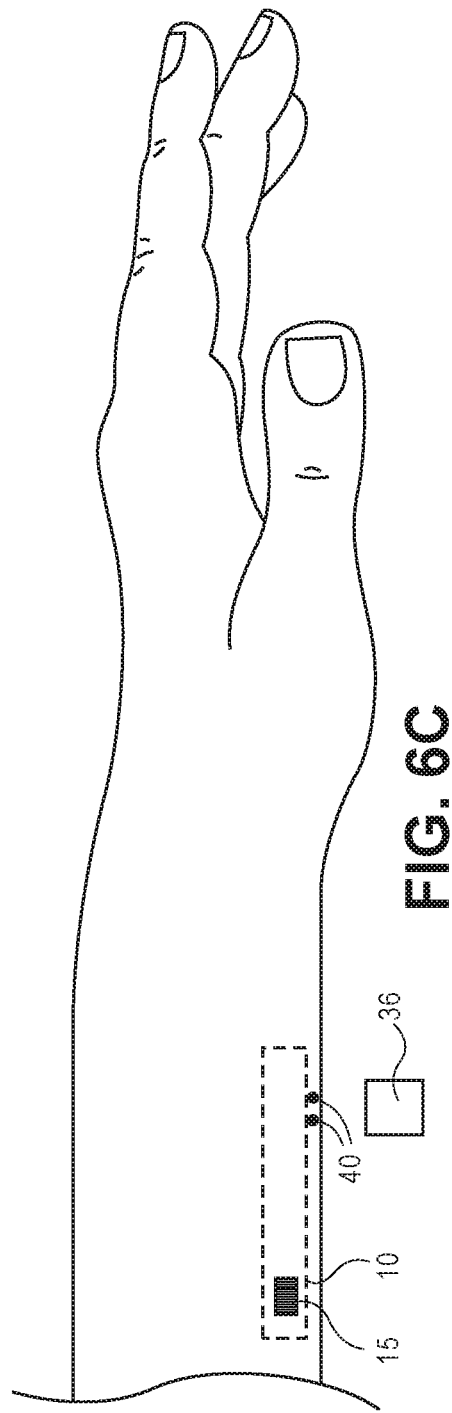

SYSTEM AND METHOD FOR DROPLET FORMATION AND MANIPULATION USING FERROFLUIDS

RELATED APPLICATION

This Application is a U.S. National Stage filing under 35 U.S.C. § 371 of International Application No. PCT/US2016/056148, filed Oct. 7, 2016, which claims priority to U.S. Provisional Patent Application No. 62/241,917 filed on Oct. 15, 2015, which are hereby incorporated by reference. Priority is claimed pursuant to 35 U.S.C. §§ 119, 371 and any other applicable statute.

STATEMENT REGARDING FEDERALLY SPONSORED RESEARCH AND DEVELOPMENT

This invention was made with Government support under Grant Number 1332275, awarded by the National Science Foundation. The Government has certain rights in the invention.

FIELD OF THE INVENTION

The technical field generally relates to methods and devices that utilize magnetic forces to generate droplets from reagents mixed with a ferrofluid. Reagents may include chemical species, nucleic acid (e.g., DNA), cells, drugs, and the like.

BACKGROUND

Lab-on-chip devices are becoming increasing explored and used in commercial applications. Typically, these devices are integrated into a microfluidic platform that utilize small volumes of reagents to transport, mix, and perform reactions that used to be performed in larger, bench-top settings. Lab-on-chip devices are known that use droplets as small reaction vessels that contain reagents and/or cells. In typical droplet-based devices, the droplets are formed by a pinching flow of oil around an aqueous phase to generate aqueous droplets or emulsions carried in an oil-based medium. In current droplet-based devices, various pumping devices (e.g., syringe pumps) are also required to pump the aqueous and oil phase components through the device to generate the emulsions. These pumps often require tuning of the flow rates to ensure that droplets of a particular size and composition are formed. Also, the bulky nature of pressure pumps or syringe pumps leads to more complex and larger devices which are less suitable for point-of-care assays as well as difficulty to simply load samples and reagents and mix them in a complete system.

More recently, ferrofluids, or fluids that contain suspended magnetic nanoparticles, have been used in many biomedical applications including various pumping and valving applications. See, Pamme, Magnetism and microfluidics, Lab Chip, 6, 24-38 (2006). For example, ferrofluids have been used as a tool for adjusting the size of droplets when magnetic fluids are applied in a T-junction and flow focusing droplet generators. See, Liu et al., Numerical and experimental investigations of the formation process of ferrofluid droplets, Microfluid Nanofluid, 11, 177-187 (2011). For example, Liu et al. have studied formation of ferrofluid droplets, the velocity field and droplet size in a pressure driven flow focusing device under influence of a uniform magnetic field. See Liu et al., Numerical study of the formation process of ferrofluid droplets, Physics of Fluids, 23, 072008 (2011). Tan et al. have also studied the effect of an external magnet (and also magnetic flux density gradient) and flow rates on droplet size in a pressure driven T-junction droplet generator. See Tan et al., Formation and manipulation of ferrofluid droplets at a microfluidic T-junction, J. Micromech. Microeng. 20, 045004, (2010). However, a need for accurate pumps for droplet generation in these pressure driven systems limits applying these droplet generators as portable devices for point-of-care applications. There is a need for an alternative droplet generating modality that can be utilized to encapsulate reagents and other constituents (e.g., cells) within droplets without the need for accompanying pumping and associated fluidic components associated with traditional droplet-based devices.

SUMMARY

In one embodiment, an emulsification or droplet generation method is disclosed that can be performed at the micro-scale using a microfluidic device and magnetic field induced movement of the fluid containing a ferrofluid therein. Using either a permanent magnet or an electromagnet, the ferrofluid is pulled through the one or more microfluidic channels that are coupled to one or more ferrofluid reservoirs. The one or more microfluidic channels lead to a continuous-phase reservoir. A step is formed at the transition from the one or more microfluidic channels to the continuous-phase reservoir and is the location where droplets are formed. The ferrofluid makes the solution susceptible to a magnetic field, creating a body force within the fluid. Therefore, by adjusting the magnetic field strength (e.g., by locating a permanent magnet, or energizing an electromagnet) one is able to draw fluid to the step interface, where surface tension leads to fluid breakup; generating droplets without using external pumps as is required for conventional methods.

In another embodiment, a method of forming droplets in a microfluidic device using a ferrofluid includes providing a microfluidic device having one or more ferrofluid reservoirs containing a ferrofluid therein and a continuous-phase reservoir containing an oil therein, wherein the one or more ferrofluid reservoirs are coupled to the continuous-phase reservoir via one or more microfluidic channels, the continuous-phase reservoir comprising a step region having an increased height as compared to a height of the one or more microfluidic channels. An external magnetic field is applied to the microfluidic device, wherein the external magnetic field moves the ferrofluid solution along the one or more microfluidic channels and generates droplets in the continuous-phase reservoir.

In another embodiment, a method of forming droplets in a microfluidic device using a ferrofluid includes providing a microfluidic device having one or more ferrofluid reservoirs containing an organic ferrofluid therein and a continuous-phase reservoir containing an aqueous solution therein, wherein the one or more ferrofluid reservoirs are coupled to the continuous-phase reservoir via one or more microfluidic channels, the continuous-phase reservoir comprising a step region having an increased height as compared to a height of the one or more microfluidic channels. An external magnetic field is applied to the microfluidic device, wherein the external magnetic field moves the organic ferrofluid solution along the one or more microfluidic channels and generates organic droplets in the continuous-phase reservoir.

In still another embodiment, a microfluidic device for forming droplets includes at least one ferrofluid reservoir disposed in the microfluidic device and containing a ferrofluid therein. The device includes a continuous-phase reservoir disposed in the microfluidic device and containing an oil phase therein. One or more microfluidic channels connect between the at least one ferrofluid reservoir and the continuous-phase reservoir, the continuous-phase reservoir comprising a step region having an increased height as compared to a height of the one or more microfluidic channels. A moveable external magnet is located adjacent to the microfluidic device.

In still another embodiment, an implantable microfluidic device for delivering a drug to a subject includes a ferrofluid reservoir disposed in the microfluidic device and containing a ferrofluid and drug therein. A continuous-phase reservoir is disposed in the microfluidic device and contains an oil phase therein, the continuous-phase reservoir containing a permeable membrane therein through which the drug passes. One or more microfluidic channels connect between the ferrofluid reservoir and the continuous-phase reservoir, the continuous-phase reservoir comprising a step region having an increased height as compared to a height of the one or more microfluidic channels. A permanent magnet is disposed adjacent to the permeable membrane on a first side of the device. An electromagnet is disposed on a second (opposite) side of the device and is connected to driver circuitry configured to power the electromagnet.

BRIEF DESCRIPTION OF THE DRAWINGS

FIG. 1A illustrates a side, schematic view of a microfluidic device according to one embodiment. FIG. 1A illustrates droplets being formed at a step in channel height due to the gradient of the magnetic field.

FIG. 1B illustrates a top view of the microfluidic device of FIG. 1A.

FIG. 1C illustrates a side view of a microfluidic device according to another embodiment. In this embodiment, which employs a parallel configuration, there are multiple microfluidic channels that connect the ferrofluid reservoir to the continuous-phase reservoir.

FIG. 1D illustrates a top view of another embodiment of a microfluidic device. In this embodiment, there are separate sample/reagent reservoirs that connect to a common microfluidic channel that leads to the continuous-phase reservoir.

FIG. 6A schematically illustrates a side view of a microfluidic device according to another embodiment that includes a porous membrane.

FIG. 6B schematically illustrates a side view of a microfluidic device according to another embodiment that includes a porous membrane.

FIG. 6C illustrates one use of the microfluidic device being implanted into the subject to deliver a drug or a medicament.

DETAILED DESCRIPTION OF THE ILLUSTRATED EMBODIMENTS

Figure 1E:
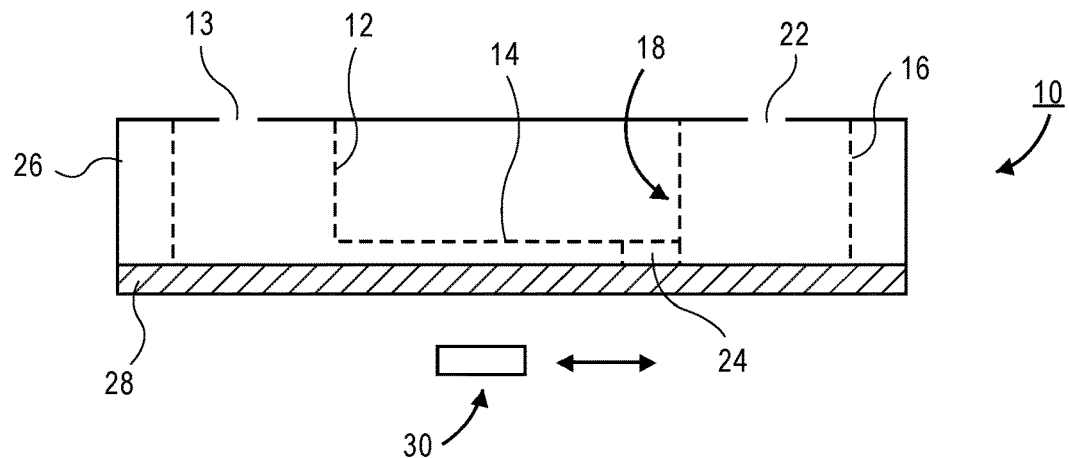
FIG. 1E illustrates a side view of a microfluidic device according to one embodiment.
Figure 1F:
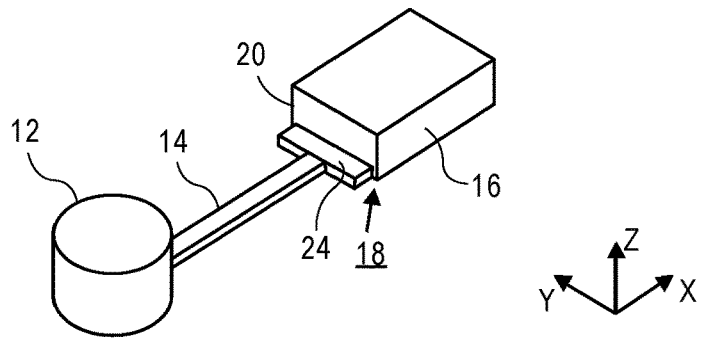
FIG. 1F illustrates a three dimensional perspective view of a ferrofluid reservoir connected to a continuous phase reservoir via a single microfluidic channel. A terraced transition region is also illustrated.

FIGS. 1A-1D schematically illustrate various embodiments of a microfluidic device 10 for forming droplets 40. The microfluidic device 10 includes at least one ferrofluid reservoir 12 that is disposed or formed in the microfluidic device 10. The at least one ferrofluid reservoir 12 contains a ferrofluid 15 or is configured to receive a ferrofluid 15. As used herein, "ferrofluid" refers to a fluid that contains magnetic nanoparticles 17 suspended therein that confers the bulk fluid with magnetic properties. The size of the magnetic nanoparticles 17 needs to be small enough such that the magnetic nanoparticles 17 do not sediment out in response to gravity. Another way of saying this is that the thermal energy is higher than the gravitational energy and magnetic energy due to an external magnetic field that would otherwise tend to cause sedimentation of the magnetic nanoparticles 17, so they remain relatively evenly dispersed throughout the fluid. The magnetic nanoparticles 17 may vary in size but the sizes are generally within a few nm in diameter to around 100 nm in diameter. The size depends on the density of the fluid and the iron content/density of the magnetic nanoparticles 17. In some embodiments described herein, the ferrofluid 15 is aqueous-based. In other embodiments, the ferrofluid is organic-based. This embodiment would be useful for example to create magnetic droplets 40 that are polymerized to form microparticles, when the pre-polymer requires an organic solvent continuous phase. An example of an aqueous-based ferrofluid 15 includes EMG 408 available from Ferrotec, Co. which includes 10 nm magnetic nanoparticles. Another example of an aqueous-based ferrofluid 15 includes concentrated Feraheme (ferumoxytol available from amag pharmaceuticals) which includes 20 nm magnetic nanoparticles. Concentrated ferumoxytol is made by centrifuging about 1 ml of ferumoxytol for 3 hours at 14,000 rpm and then the top 300 µl was removed to make the solution more susceptible to a magnetic field. Magnetic nanoparticles 17 in ferumoxytol are coated with polyglucose sorbitol carboxy-methyl ether which is a sugar and makes it a good choice for applications where direct contact of other materials with iron could cause problems.

In some embodiments there may be a single ferrofluid reservoir 12 such as illustrated in FIG. 1A while in other embodiments there are multiple ferrofluid reservoirs 12. FIG. 1A illustrates a mixture of the ferrofluid 15 and a sample 2 being loaded into the ferrofluid reservoir 12. The sample 2 may include a reagent, environmental sample, a biological fluid (e.g., bodily fluid), or even a cell-containing sample. The ferrofluid 15 and sample 2 may be pre-mixed or, as explained herein, the sample 2 and the ferrofluid 15 can be mixed prior to emulsifying of the sample 2 on the microfluidic device 10 by simply applying the sample to the reservoir (e.g., by pipetting, capillary insertion, pouring) followed by mixing of the ferrofluid 15 and sample 2 by oscillating or lateral motions of an external magnet 30. FIG. 1D illustrates an embodiment where three ferrofluid reservoirs 12a, 12b, 12c are used. One reservoir 12a contains a ferrofluid mixed with a first reagent (or sample). A second reservoir 12b contains a ferrofluid mixed with a second reagent (or sample). A third reservoir 12c contains a ferrofluid mixed with a third reagent (or sample).

The ferrofluid reservoir 12 may have a variety of different volumes. For example, the ferrofluid reservoir 12 may contain microliter or even milliliter sized volumes of ferrofluid 15. The ferrofluid reservoir 12 may include an inlet 13 or opening that is used to fill (or re-fill) the ferrofluid reservoir 12 as seen in FIG. 1E. In some instances the inlet 13 can be open or exposed to the external environment so that it can be readily filled. In other embodiments, the inlet 13 can be covered or sealed after being filled with ferrofluid 15. In yet another alternative, the inlet 13 can be fluidically coupled to a source of fluid using tubing or the like.

Still referring to FIGS. 1A-1D, one or more microfluidic channels 14 are coupled to the ferrofluid reservoir 12 and are used to transport ferrofluid 15 to a droplet generation region as described herein. The one or more microfluidic channels 14 may have varying lengths but they are typically greater than 100 µm (e.g., 700 µm). In one embodiment, a single microfluidic channel 14 can lead from a single ferrofluid reservoir 12 as seen in FIGS. 1A and 1B. Alternatively, multiple microfluidic channels 14 can lead from a single ferrofluid reservoir 12 as is illustrated in FIG. 1C. This latter construction enables parallel processing so that large numbers of droplets 40 can be created and collected. The cross-sectional shape of the microfluidic channels 14 are typically rectangular or square and have widths and heights on the order of tens of microns. For example, an exemplary width of the microfluidic channel 14 may be on the order of around 65 µm with a height on the order of around 30 µm, although other dimensions may be used.

Figure 2:
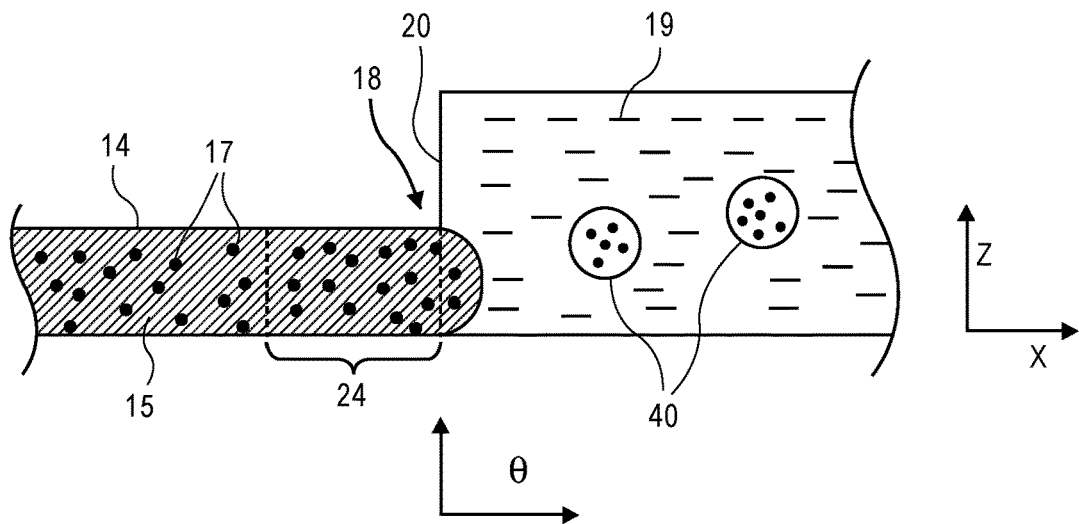
FIG. 2 illustrates a close-up side schematic view of the intersection between a microfluidic channel and the stepped region of the continuous phase reservoir.

The one or more microfluidic channels 14 carry the ferrofluid 15 from the ferrofluid reservoir 12 to a downstream continuous phase reservoir 16. The continuous phase reservoir 16 contains the continuous phase fluid 19 in which the droplets are formed. In one embodiment, the continuous phase reservoir 16 is filled with an oil-based continuous phase fluid 19 while the ferrofluid 15 is aqueous-based. Alternatively, the continuous phase reservoir 16 may be filled with an aqueous-based continuous phase fluid 19 while the ferrofluid 15 is organic or oil-based. The continuous phase reservoir 16 includes a step region 18 wherein the height of the one or more microfluidic channels 14 transitions to a larger height of the continuous phase reservoir 16. As explained herein, droplets 40 are formed at or adjacent to this step region 18. Referring to FIG. 2, a step or wall 20 is formed that extends generally transversely to the longitudinal axis of the one or more microfluidic channels 14. The angle of the step or wall 20 may be formed with an angle θ that is equal to or less than 90°. The angle may be less than 90° although at lower angles closer to 0° droplets will not readily form. The continuous phase reservoir 16 has a height that is much larger than the height of the microfluidic channels 14 that lead thereto. For example, the height of the continuous phase reservoir 16 may typically be within the range of 125-200 µm (e.g., 170 µm), although heights outside this range may also be used. Likewise, the width of the continuous phase reservoir 16 is much larger than the width of the microfluidic channels 14 that lead thereto. The larger width and height of the continuous phase reservoir 16 produces a chamber or region with a large volume that can accommodate a large number of droplets or emulsions that are formed in the device as described herein. The continuous phase reservoir 16 may include an outlet 22 (seen in FIG. 1E) that is used to extract the droplets or emulsions. The outlet 22 can also be used to back-fill the device with the continuous phase (e.g., oil). In some embodiments, the outlet 22 is open or exposed to the external environment. In other embodiments, the outlet 22 may be sealed such as with a layer of PDMS to seal the outlet 22.

With reference to FIGS. 1A-1F and FIG. 2, in one preferred embodiment, the one or more microfluidic channels 14 lead first to a terraced or transition region 24 prior to entering the continuous phase reservoir 16. The terraced or transition region 24 has a height that is the same as the microfluidic channel 14 that leads to the terraced or transition region 24 but a width that extends to the approximately same width as the downstream continuous phase reservoir 16. The length of the terraced or transition region 24 is less than about 100 µm (e.g., 60 µm or 90 µm are exemplary lengths). The fluid that enters the terraced or transition region 24 is able to expand in the x-y direction. Once the fluid enters the continuous phase reservoir 16 the fluid can expand in the z direction to form the droplet or emulsion. It should be appreciated that the terraced or transition region 24 is optional and may be omitted entirely.

The microfluidic device 10 may be fabricated using conventional protocols for making polymer-based microfluidic devices such as polydimethylsiloxane (PDMS)-based microfluidic devices. For example, the ferrofluid reservoir(s) 12, the microfluidic channel(s) 14, and the continuous phase reservoir 16 may be formed in PDMS using soft lithography methods (e.g., using photoresist and bonded class slides or coverslips to form a mold) and the elastomeric portion 26 device may be bonded to a glass substrate 28 (e.g., glass slide or cover slip) using oxygen plasma treatment or an optically cured adhesive (e.g., NOA 81; Norland Products, Inc., Cranbury, N.J.) as illustrated in FIG. 1E. The inlet 13 and outlet 22 may also be formed by using a punch in the elastomeric PDMS layer 26. In some embodiments, the inlet 13 and the outlet 22 may be open to the external environment. In other embodiments, the inlet 13 and/or the outlet 22 may be covered by another layer of PDMS (not illustrated in FIG. 1E).

Referring to FIG. 1E, FIGS. 3A-3B, and FIG. 4, the microfluidic device 10 includes, as one embodiment, a moveable external magnet 30 that can be positioned adjacent to the underside of the microfluidic device 10 to drive the ferrofluid 15 through the microfluidic device 10. The moveable external magnet 30 can be positioned at various locations as described herein to achieve different droplet generation rates as well as start and stop droplet generation as desired. In one embodiment, a permanent magnet can be used as the moveable external magnet 30 (e.g., D68 grade N52 cylindrical magnet from K&J Magnetics, Inc.). The moveable external magnet 30 can be mounted on a moveable stage or track 32 that is computer-controlled and can move laterally adjacent to the microfluidic device 10. The moveable stage or track 32 moves the magnet 30 in the x direction of FIG. 3A. In some embodiments, the moveable stage or track 32 can move magnet in the y direction and the z direction. The moveable external magnet 30 is preferably located underneath the microfluidic device 10 and is located close enough to impart a magnetic field to the ferrofluid 50 to effectuate movement of the same. In one aspect, the moveable external magnet 30 is immediately adjacent or in slight contact with the substrate 28 of the microfluidic device 10. A small gap may exist, however, between the magnet 30 and the substrate 28.

To fit in a handheld format, the microfluidic device 10 could sit on top of a track 32 that holds a moveable permanent magnet 30; whereby the position of the magnet 30 can be electronically controlled, initially located below the ferrofluid reservoir 12 and moving back and forth to mix the sample and ferrofluid 15, then the magnet 30 can be electronically controlled to move down the track 32 pulling ferrofluid 15 through the microfluidic channel 14 and into the step emulsification region 18 to generate droplets 40.

As an alternative to the track 32, the permanent magnet 30 may be affixed to a stage or one or more actuators. A fast z-direction motion of the magnet 30 on the track 32, stage or actuator (or other movement device) away from the microfluidic device 10 can stop the motion of droplets 40 quickly. The magnet 30 could then be removed (or moved) from the region of the continuous phase reservoir 16 to allow imaging (fluorescence or spectrophotometric, or colorimetric) of a reaction occurring in the droplets 40, the magnet 40 could also be moved more slowly to pull droplets 40 following generation into an analysis region located downstream of the continuous phase reservoir 16 for optical or electronic analysis drop-by-drop. Alternatively, the imaging system could direct imaging illumination and collect light from a different direction as the magnet 30, and the magnet 30 could be held in place to ensure minimal motion of droplets 40 during imaging.

In one embodiment, the microfluidic device 10 can be pre-loaded with oil (and optionally surfactant in certain embodiments) in the continuous phase reservoir 16 and ferrofluid 15 with reagent or sample in the ferrofluid reservoir 12, such that only a single sample addition is required to perform an assay. In order to perform multistep assays or combine reactive reagents in a timed manner another embodiment of the invention includes a plurality of inlet reservoirs as seen in FIG. 1D each with some amount of ferrofluid 15 to enable driving the motion of the flow, but with different reagent or sample components. The microfluidic channels 14 extending from different reservoirs 12a, 12b, 12c can then be merged immediately prior to the emulsification junction or some distance upstream. The channels extending from the different reservoirs could all merge at one point or sequentially merge if it is desired to sequentially add reagent or sample in a desired order. In a related embodiment, ferrofluid 15 from a plurality of reservoirs 12 are merged into an intermediate reservoir following the motion of a magnet 30, followed by mixing and/or an incubation step for a controlled time period, and subsequently followed by droplet generation by a second motion of a magnet 30, 36 to draw ferrofluid 15 to a step region 18 as explained herein.

The position of the moveable external magnet 30 as well as the displacement of the same may be adjusted or altered depending on the particular application. Typically, the moveable external magnet 30 is held stationary during at least part of the droplet formation process. By being held stationary, the magnetic field remains constant and droplets 40 are generated at a substantially uniform rate. However, as explained herein, the rate of droplet formation can be altered by adjusting the relative x position of the moveable external magnet 30. The formation of droplets 40 may also be stopped by moving the moveable external magnet 30 away from the microfluidic device 10 (e.g., in the z direction) or by moving the external magnet 30 in the x direction sufficiently such that the ferrofluid 15 is not drawn toward the droplet generation. In addition, in some embodiments, the moveable external magnet 30 may be positioned beneath the ferrofluid reservoir 12 and is moved back-and-forth under the ferrofluid reservoir 12. This process may be used to mix the ferrofluid 15 and the sample.

Figure 4:
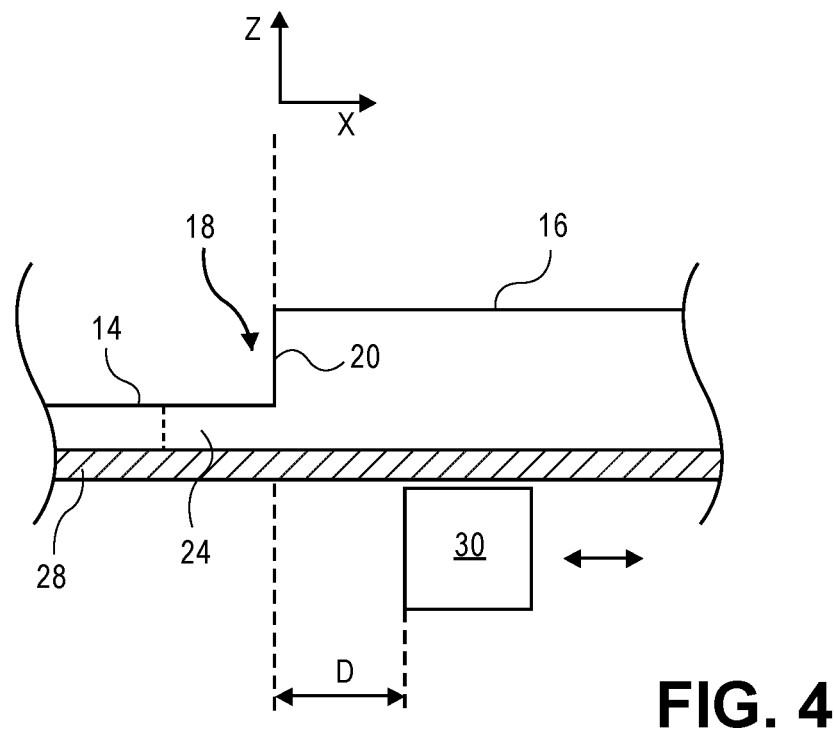
FIG. 4 illustrates an external permanent magnet being placed a distance (D) from the step of the continuous phase reservoir.

In order to generate droplets 40, the moveable external magnet 30 is moved beneath the continuous phase reservoir 16 and held stationary to begin emulsifying the sample. In this embodiment, the moveable external magnet 30 is moved along a track in the x direction and is then held stationary to enable the formation of droplets 40. The particular distance at which the moveable external magnet 30 is held stationary under the continuous phase reservoir 16 may vary depending on the desired droplet formation rate. The distance (D) of the external magnet 30 is measured with respect to the step or wall 20 to the closest edge or face of the external magnet 30 as seen in FIG. 4. It has generally been found that higher droplet formation rates are achieved when this separation distance between the step or wall 20 and the external magnet 30 is small. Larger separation distances produce lower droplet generation rates. The external magnet 30 is generally located a distance (D) that is less than about 0.5 cm from the step or wall 20 and more preferably less than 0.25 cm from the step or wall 20.

Figure 5A:
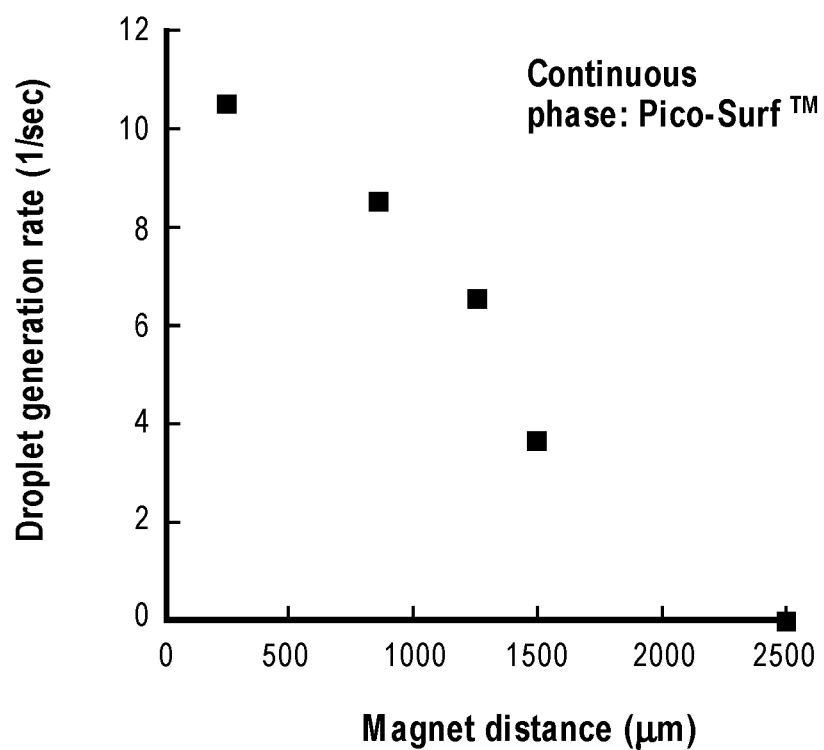
FIG. 5A illustrates a graph showing the droplet generation rate of the microfluidic device as a function of magnet distance (D) for experiments using Pico-Surf™ as the continuous phase.
Figure 5B:
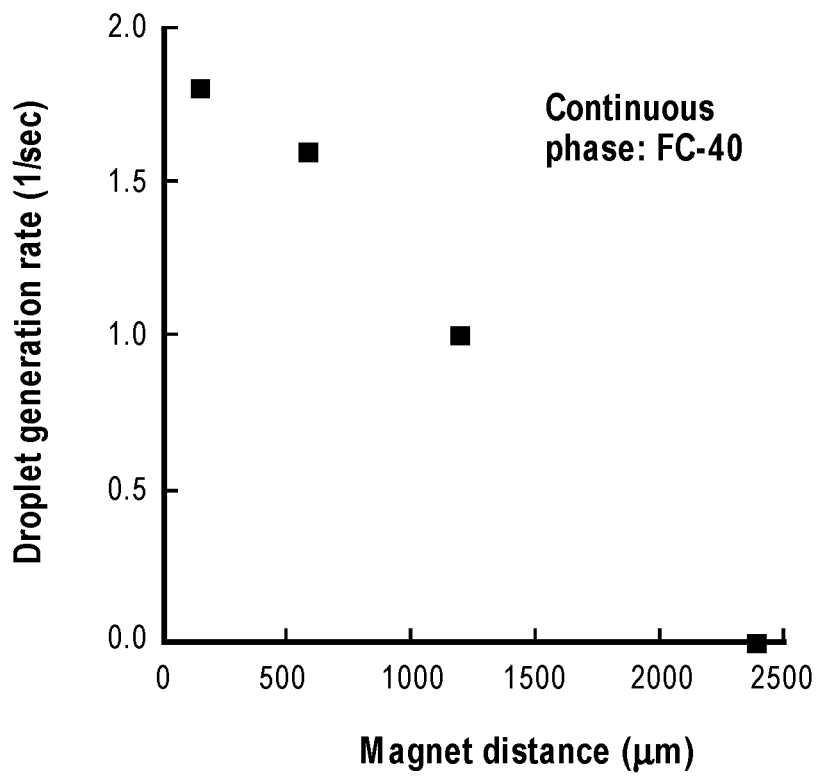
FIG. 5B illustrates a graph showing the droplet generation rate of the microfluidic device as a function of magnet distance (D) for experiments using FC-40 as the continuous phase.

FIGS. 5A and 5B illustrate the droplet generation rate that was obtained at various magnet distances (D) using both Pico-Surf™ (FIG. 5A) and FC-40 (FIG. 5B) as the continuous phase. Increases in droplet generation rate are seen for magnet distances (D) that are less than 0.25 cm. Of course, it should be understood that these distances were observed using an external magnet 30 with a particular size and strength. Different distances can be expected based on external magnets 30 of differing magnetic strengths.

Figure 3A:
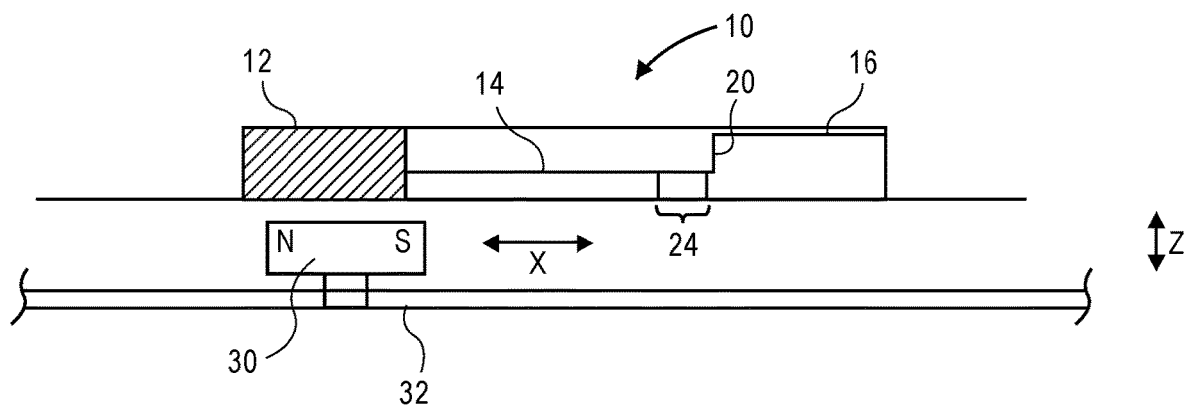
FIG. 3A illustrates an embodiment of a stage or track that is used to move an external permanent magnet to various positions in the x direction relative to the microfluidic device. The magnet may also be moved in the z direction.
Figure 3B:
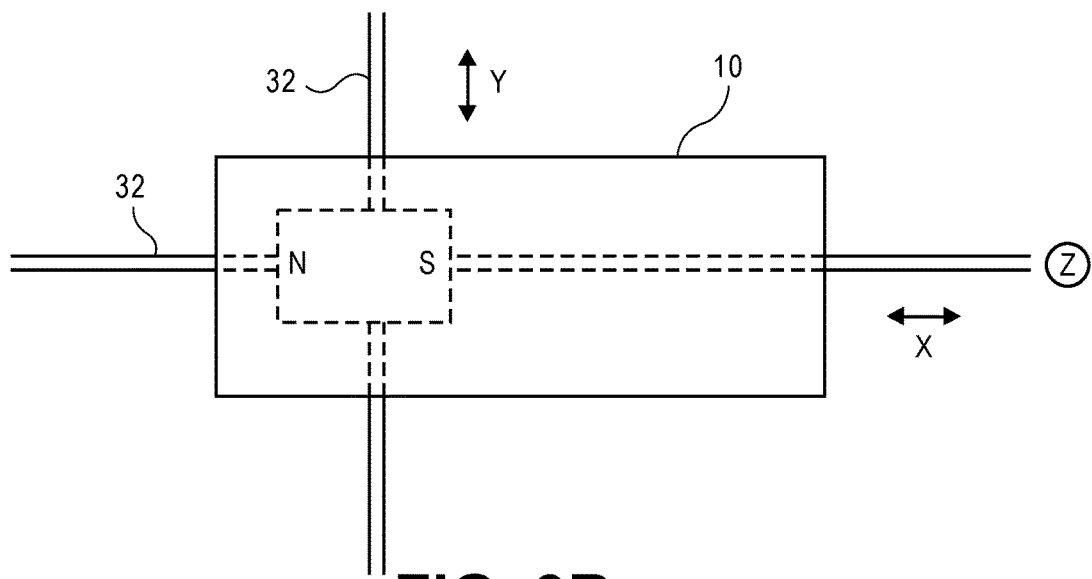
FIG. 3B illustrates an embodiment of a stage or track that is used to move an external permanent magnet to various positions in the x and y direction relative to the microfluidic device. The magnet may also be moved in the z direction.
Figure 3C:
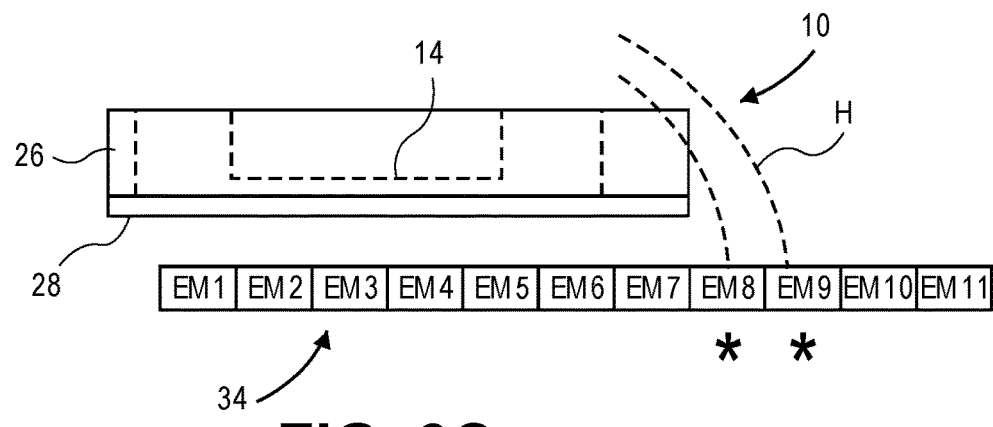
FIG. 3C illustrate an embodiment of a microfluidic device that is used with one or more electromagnets to apply an external magnetic field H to the microfluidic device.

After formation of the droplets 40, the stage or track device 32 may move in the x, y, or z directions for post-formation manipulation. For example, movement in the z direction can be used to rapidly remove the magnetic field from affecting the droplets 40 or ferrofluid 15 in the device 10. For instance, droplet 40 movement may be stopped by moving the moveable external magnet 30 away from the microfluidic device 10 in the z direction. As an alternative to using a permanent magnet, an electromagnet 34 (or multiple electromagnets) could be used as the moveable external magnet 30 as seen in FIG. 3C. For example, different electromagnets 34 or sections (EM1-EM11) could be activated (denoted by *) to provide for a moveable magnetic field H that can be used to drive the ferrofluid 15 through the microfluidic device 10.

FIG. 6A illustrates another embodiment of the microfluidic device 10. In this embodiment, an elastomeric portion 26 (e.g., PDMS) is bonded to a substrate 28 to define the ferrofluidic reservoir 12, the microfluidic channel 14, and the continuous phase reservoir 16. Note that in this embodiment, ferrofluidic reservoir 12 is completely contained in the elastomeric portion 26 and is pre-loaded with ferrofluid 15. Likewise the continuous phase reservoir 16 is pre-loaded with the continuous phase fluid (e.g., aqueous-based fluid or oil-based fluid). In this embodiment, a porous membrane 50 is defined in a region of the continuous phase reservoir 16. The porous membrane 50 contains pores therein that permit the selective passage of droplets 40 in response to a force that urges the droplets 40 through the porous membrane 50 to the opposing side. In the embodiment of FIG. 6A, the opposing side of the porous membrane 50 contains a second phase 52 which may be a solution or fluid into which the droplets 40 pass or merge into. In some instances, the second phase 52 may include a gas such as ambient air. For example, droplets 40 can still pass through the porous membrane 50 even without a liquid fluid located on the opposing side of the porous membrane 50.

The porous membrane 50 may be a PTFE or Nylon membrane having micrometer-sized pore sizes. An exemplary porous membrane 50 may include a Nylon membrane having 5 micron pore sizes available from BioDesign, Inc., Carmel, N.Y. The porous membrane 50 acts as a filter membrane that is incorporated into the microfluidic device 10 and is in fluid communication with the continuous phase reservoir 16. Operation of this embodiment of the microfluidic device 10 is similar to other embodiments where a moveable external magnet 30 is first placed adjacent to the microfluidic device 10 to generate droplets 40. The generated droplets 40, which have a known volume, can then be drawn out of the continuous phase reservoir 16 using a magnet 36. The magnet 36 may be the same moveable external magnet 30 or a different magnet entirely. The magnet 36 may be a permanent magnet or an electromagnet. The porous membrane 50 acts as a passive valve that prevents the release of the droplets 40 until a change in the magnetic field is induced in the system to overcome the interfacial energy increase that is needed to pull droplets 40 through the porous membrane 50. The Nylon membrane 50 is hydrophilic allowing only ferumoxytol to pass through the membrane 50 and oil cannot pass. Other membranes 50 with different properties could also be used.

The embodiment of FIG. 6A could be used, for example, as a drug or medicament delivery device 10 that selectively delivers medicine to a subject as illustrated in FIG. 6C (it should be understood that the device 10 may be located in other anatomical spaces). The microfluidic device 10 could be implanted within a patient (e.g., intramuscularly or subcutaneously) and pre-loaded with the drug and ferrofluid 15. In some embodiments, the magnetic nanoparticles 17 that form the ferrofluid 15 act as the drug and no separate drug is needed. An example of this is ferumoxytol. In still other embodiments, a drug may be conjugated to the magnetic nanoparticle 17 (e.g., doxorubicin). In other embodiments, a separate drug is mixed within the ferrofluid 15 and is captured in the formed droplets 40. An externally applied magnetic field can be used to first generate the droplets 40 containing the drug or medicament. A second or different externally applied magnetic field can then be applied to pull the generated droplets 40 through the porous membrane 50 where they enter the second phase 52. The second phase 52 may include bodily or interstitial fluids into which the droplets 40 dissolve or merge; thereby releasing the drug or medicament contained in the droplets 40. This particular embodiment is advantageous because it permits dosing over a large dynamic range as one can control the amount of very finely quantized volumes of droplets 40 (e.g., picoliters to nanoliters per droplet) that are pulled or forced through the porous membrane 50. Further, this can be accomplished as needed through feedback with a sensing system integral with the device 10 or on demand by the user or other health care professional. In addition, this embodiment of the microfluidic device 10 permits localized delivery of drugs. Enough drug or medicament mixed with a ferrofluid may be pre-loaded into the implanted microfluidic device 10 such that drug can be delivered over an extended period of time (e.g., weeks or months) without exhausting the supply of drug. Furthermore, the embodiment of FIG. 6A could be used in a wearable format for transdermal drug delivery. Pores could be created in the skin using microneedles, iontophoresis, or other mechanisms, then controllable drug release could be performed when the released droplets 40 containing drugs from the porous membrane 50 are in contact with the pores created in the skin. In this case, there is no need for injection using large needles.

The embodiment of FIG. 6C could be used for controlled delivery of reagents or drugs containing magnetic nanoparticles 17 by implanting the device 10 preferably near the skin where a magnetic field could be easily applied externally. In addition, by incorporating a small permanent magnet on top of the membrane 50 for releasing droplets 40, the device 10 could be implanted anywhere in the body and the drug could be released intermittently using a programmed schedule or being activated remotely using a wireless controller.

One possible drug could be ferumoxytol that is used for treatment of iron deficiency. Ferumoxytol containing droplets 40 can be generated with or without a surfactant. If surfactant is not used, after the desired numbers of droplets 40 are formed, the droplets 40 can coalesce after a few minutes and then these droplets 40 are transferred to the second phase (e.g., the bodily fluid bathing or surrounding the device 10) by applying magnetic force such that the coalesced-droplets 40 could pass through the porous membrane 50 easier. To avoid undesired release of the drug by other external magnetic fields the distance between the ferrofluid reservoir 12 and the porous membrane 50 could be adjusted so that while droplets 40 are squeezing through the porous membrane 50 no more droplets 40 are generated at the terrace region 22. Different sections of the device 10 could also be coated with different materials. For example, the inlet region of the device 10 could be coated with another layer of polymer, etc. so that it acts as a diffusion barrier and the drug will not diffuse into the body over time. These coatings could be applied to other regions of the device 10.

In still another embodiment, the microfluidic device 10 may include geometrically designed microfluidic channels 14 and possible intermediate chambers or reservoirs to thereby make the process of droplet release dependent on the spatial and temporal location of the external magnets 30, 36 for more controllability. That is, a predefined sequence of magnetic field directions and strengths would be needed to release drug-containing droplets 40 that would not be likely to exist in normal daily events. For implanting the microfluidic device 10, the ferrofluid reservoir 12 may be sealed which could be done by clamping or bonding another PDMS layer (or other polymers and materials) from the top once the drug is loaded in the microfluidic device 10.

FIG. 6B illustrates an alternative embodiment of the microfluidic device 10 that incorporates the porous membrane 50. In this embodiment, there is another layer or substrate 54 that is situated atop the microfluidic device 10 and defines a chamber 56 for collecting the droplets 40 that are generated in the microfluidic device 10. In one aspect, this chamber 56 may be removed from the microfluidic device 10 so that the droplets 40 can be transported for further processing or analysis. Alternatively, the chamber 56 may be connected to one or more additional microfluidic channels (not shown) that are integrated as part of the microfluidic device 10 so that the droplets 40 can be delivered for downstream reaction or analysis which is useful for point-of-care applications. The droplets 40 are created in the same manner as described above and a magnet 36 is used to pull the droplets 40 into the chamber 56.

In the embodiments of FIGS. 6A and 6B, since droplet generation is very controllable using this system, one can emulsify a certain volume of a sample into droplets 40 and then release it to another phase by forcing or squeezing it through the porous membrane 50 by applying magnetic force over time. This can all be done without traditional displacement or vacuum pumps which are difficult to miniaturize for applications for example in precise continuous and dosed drug delivery.

Figure 6D:
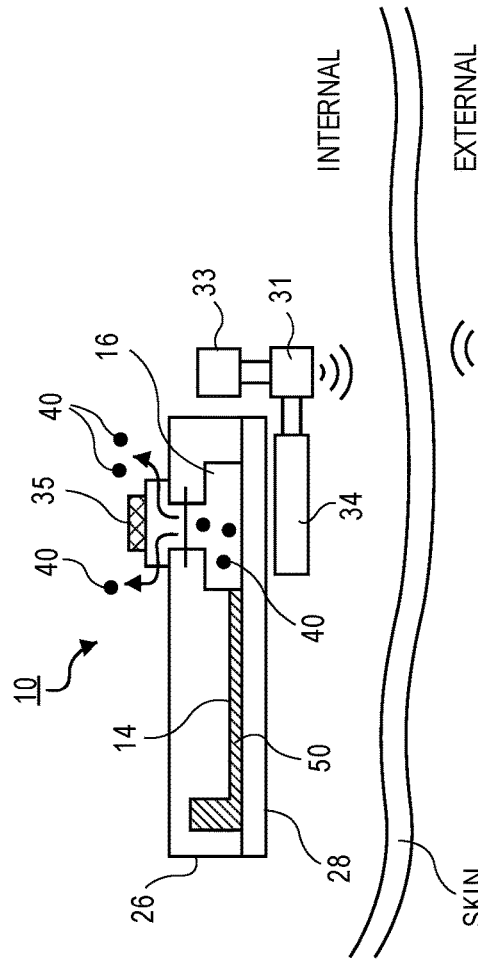
FIG. 6D illustrates another embodiment of an implantable microfluidic device that is used to deliver a drug or a medicament to a subject.

FIG. 6D illustrates one embodiment of an implantable device 10 that can be implanted inside the body of a subject (e.g., mammal). The device 10 is similar to that described above with respect to FIGS. 6A and 6C in that a porous membrane 50 is provided that is permeable to droplets 40 that contain a drug or medicament and a ferrofluid which can then leave the device 10 and be delivered to the patient. In this embodiment, an electromagnet 34 is located adjacent the device 10 and is connected to driver circuitry 31 that is powered via an internal power source 33 such as a battery. A permanent magnet 35 is located above or adjacent (on an opposing side of the device 10 as the electromagnet 34) to the porous membrane 50 to provide a pulling force that pulls the droplets 40 from the continuous phase reservoir 16 through the porous membrane 50 where the droplet 40 are exposed to the bodily fluids or tissue of the subject so that the drug is released into the subject.

In one embodiment, the driver circuitry 31 may be pre-programmed to generate droplets 40 containing a drug a pre-defined times or intervals. In another embodiment, a wireless controller 37 that is located external to the subject can be used to control the generation of droplets 40 by actuating the electromagnet 34. Actuation may either be manual or automatic. In this regard, drug containing droplets 40 may be released into the subject at specified intervals or times as well as delivering the desired dosage amount by adjusting the length of time that electromagnet 34 is in the ON state. Leaving the electromagnet in the ON state for a longer period of time will generate more droplets 40. When the electromagnet 34 is turned to the OFF state, the magnetic force from the permanent magnet 37 pulls the generated droplets 40 through the permeable membrane 50 where they exit the device 10 and are delivered locally to the subject.

Figure 6E:
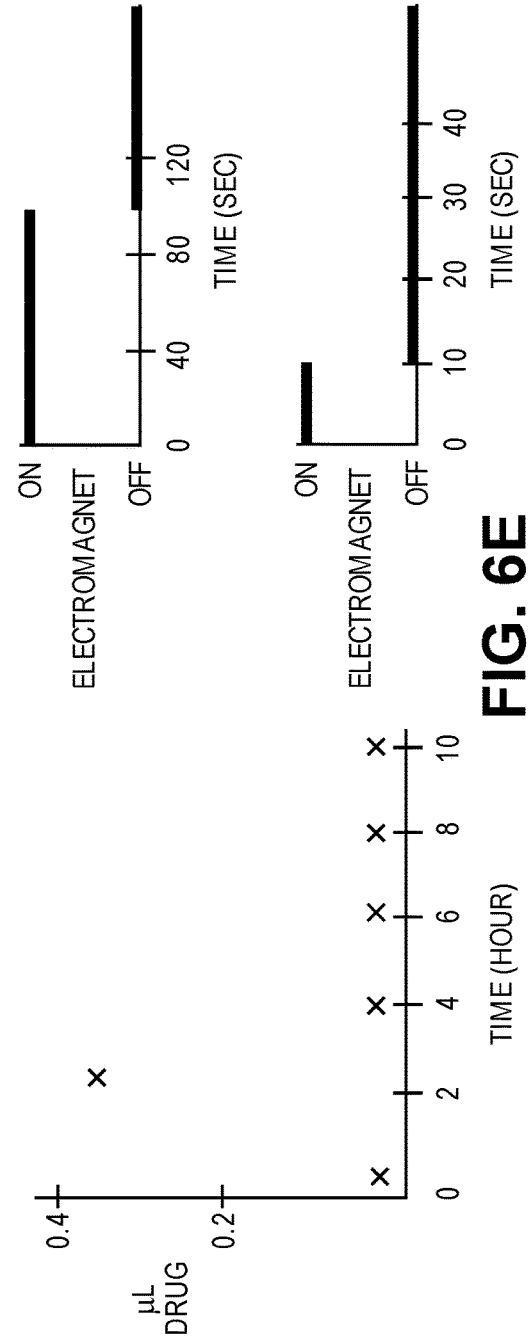
FIG. 6E illustrates a graph showing the volume of delivered drug at selected time intervals using an implantable microfluidic device of the type illustrated in FIG. 6D. Also illustrated is a graph showing the ON/OFF status of the electromagnet used to deliver a "low" dose of a drug or a "high" dose of a drug.

FIG. 6E illustrates how the device 10 of FIG. 6D may be used to generate a consistent dosage of drug using droplets 40 by periodically generating droplets 40 at different time intervals by energizing the electromagnet 34 for a fixed period of time. In this example, a "low" dose of drug is delivered by energizing the electromagnet 34 for a period of around 10 seconds. After the 10 second period has elapsed, the electromagnet 34 is then turned to the OFF state and the droplets 40 are then pulled out of the device 10 using the permanent magnet 35. FIG. 6E also illustrates a data point at the two hour time period where the electromagnetic 34 was energized for over 100 seconds which produces a "high" dosage of the drug due to more droplets 40 being formed. After the electromagnetic 34 is turned to the OFF state, the droplets 40 exit the device 10 by being pulled through the porous membrane 50 via the permanent magnet 35.

Figure 7:
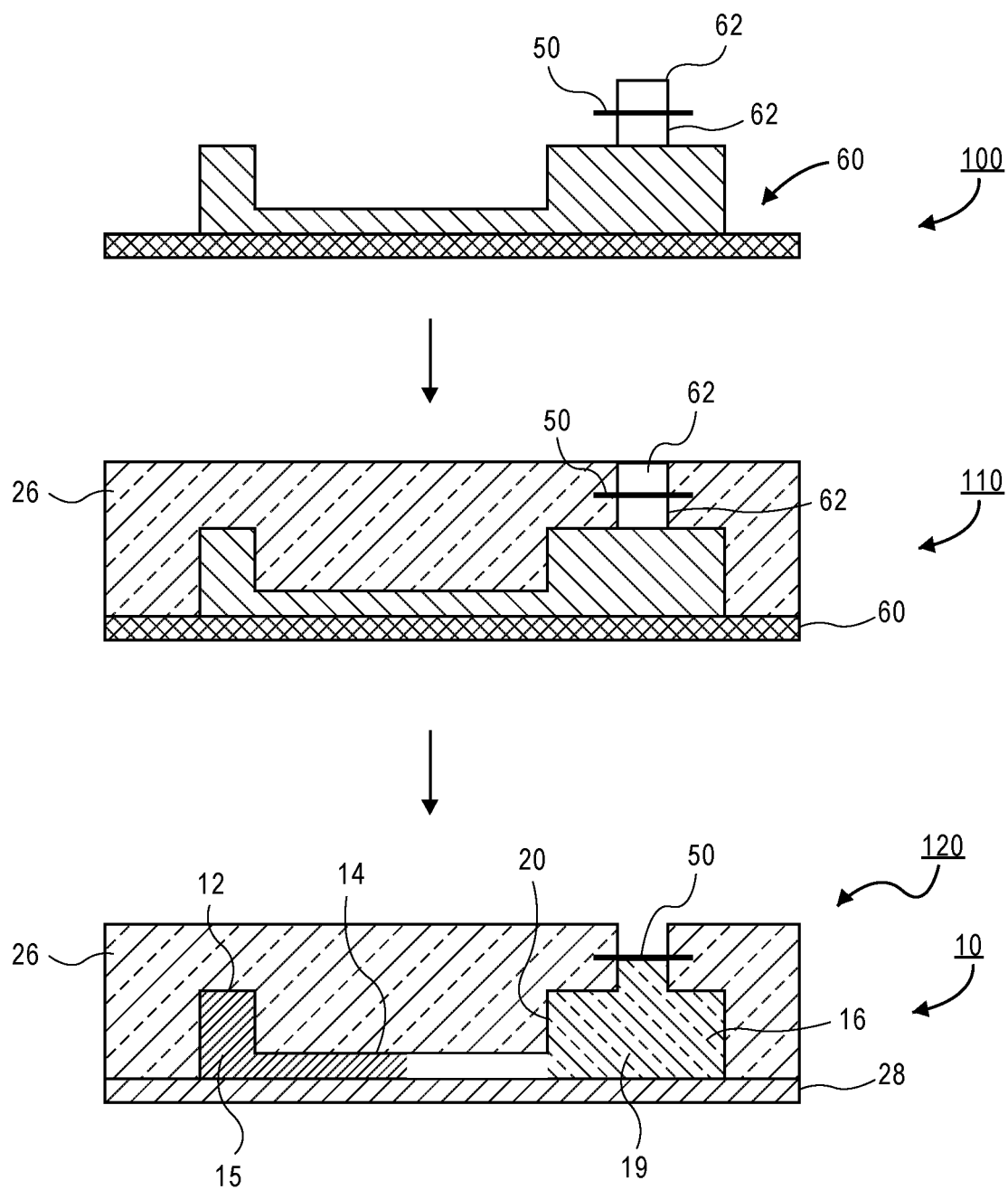
FIG. 7 illustrates a method of making a microfluidic device according to one embodiment.

FIG. 7 illustrates an operation for making the microfluidic devices 10 according to one embodiment. FIG. 7 illustrates a method of making the microfluidic device 10 of FIGS. 6A and 6B, although it should be understood that a similar manufacturing method may be used to make other embodiments that do not incorporate the porous membrane 50. As seen in operation 100, a mold 60 is provided that defines the contours of the ferrofluid reservoir 12, microfluidic channel(s) 14, and continuous phase reservoir 15. The mold 60 may be made from a material such as silicon and photoresist and may be formed using conventional lithography techniques. In addition, for this embodiment, two permanent magnets 62 are placed on the mold as indicated and sandwich a sheet or disc of material that forms the porous membrane 50 interposed between both magnets 62. The porous membrane 50 may be hydrophilic or hydrophobic depending on the particular need. The pore dimensions of the porous membrane 50 may vary from about 0.1 microns to a few 100 microns. As explained herein, a PTFE or Nylon membrane 50 having a pore size of 5 microns may be used. The porous membrane 50 is pinched between two relatively strong permanent magnets 62 (e.g., B6301 available from K&J Magnetics, Inc.) during the fabrication process. The purpose of the magnets 62 pinching to the porous membrane 50 is to avoid wetting of the porous membrane 50 with the liquid polymer (described below) that is then poured over the structure.

After the magnets 62 containing the porous membrane 50 are placed in the desired location over the continuous phase reservoir 16 location, PDMS (or other curable polymer) that is mixed with a curing agent is gently poured over the mold 60 and the sandwich structure formed by the magnets 62 and the porous membrane 50. The porous membrane 50 is held in a horizontal position during this process. Next, the mold 60 and PDMS structure is placed in an oven for about five hours at 65° C. to cure to create the PDMS structure or layer 26. The end result of this process is illustrated by operation or step 110 in FIG. 7. Next, the PDMS structure 26 is cut away from the mold 60 and the two magnets 62 are removed from the top and bottom of the porous membrane 50 and the PDMS structure 26 and an access passageway or hole is formed in the PDMS structure 26 to enable filling the ferrofluid reservoir 12. The PDMS structure 26 is then bonded to a substrate 28 (e.g., glass slide for certain embodiments). The final device is illustrated in operation 120 and incorporates the porous membrane 50 in a top region of the continuous phase reservoir 16. As an alternative to forming the ferrofluid reservoir 12 using the mold 60, the ferrofluid reservoir 12 could be formed using a punching tool (not shown) that generates the ferrofluid reservoir 12 in the PDMS layer 26. After filing the ferrofluid reservoir 12 a smaller patch of PDMS (not shown) may be applied over the hole or access passageway to seal the ferrofluid reservoir 12.

To use the microfluidic devices 10, portions of the device may need to be first treated to alter their surface chemistry. For example, surfaces of the continuous-phase reservoir 16 may be treated for a certain time with an appropriate solution or chemistry to become hydrophobic or fluorinated before introducing the oil in the continuous-phase reservoir (or hydrophilic when the continuous phase is water). For example, for oil-based solutions in the continuous-phase reservoir 16, the surfaces may be pre-treated with RAIN-X® (for Pico-Surf™ based surfactant/oil solution) or trichlorolJ1H,1H,2H,2H-perfluorooctyl) silane (Sigma Aldrich) (for FC-40, Fluorinert). For an embodiment that uses an oil-based fluid in the continuous-phase reservoir 16, the oil-based fluid is introduced via the outlet 22 and into the continuous-phase reservoir 16. The oil-based fluid may include a mixture of a surfactant that is contained in a fluorocarbon carrier oil. For example, Pico-Surf 1™ which includes 2% or 3% surfactant in Novec™ 7500 may be used (available from Dolomite Microfluidics, catalog numbers 3200211 and 3200214). Yet another example of an oil-based fluid includes FC-40 or Fluorinert™ (available from Sigma-Aldrich, catalog number F9755). Of course, these specific types of fluids are exemplary and other oil-based fluids may be used. In some embodiments, to avoid trapping of bubbles inside the continuous phase reservoir 16, the ferrofluid reservoir 12 can be covered for dead-end filling (either by another layer of PDMS bonded or clamped from the top or simply by pressing that region). The ferrofluid 15 is then loaded into the one or more ferrofluid reservoirs 12 after loading with the microfluidic device 10 with the oil phase. As explained herein, the ferrofluid 15 may include a reagent or sample therein that is intended to be encapsulated or entrained in the droplets or emulsions 40. In some embodiments, the ferrofluid reservoir 12 may also be covered with another layer of PDMS or a substrate 54 like that illustrated in FIG. 6B in order to completely enclose the microfluidic device 10. Droplets 40 will still form and negative pressure created at the ferrofluid reservoir 12 does not prevent droplet formation. In this format, by applying a magnetic field (as explained below) a certain number of droplets 40 are formed and backflow of the continuous phase stops droplet generation. To continue droplet 40 generation, the magnet 30 is moved away from the step region 20 temporarily and then relocated at the step again. This approach may be used to control the number of droplets 40 that are released so as to avoid undesired release of reagents which may be particularly suited for the microfluidic device 10 embodiment of FIG. 6C.

The moveable external magnet 30 is then moved using the stage or track 32 to the desired distance (D) away from the step 20 to initiate droplet generation. For example, the external magnet 30 is brought adjacent to the bottom of the microfluidic device 10 (if not already positioned there) and the distance of the external magnet 30 from the step or wall 20 is adjusted from 0 to about 2,500 μm downstream (x direction) of the step or wall 20. Alternatively, if one or more electromagnets 34 are used, the various electromagnets 34 or sections are energized to mimic a magnetic field to drive the ferrofluid 15. As the fluid reaches the step region 18, it starts to pinch off due to surface tension effects and droplets 40 are formed.

Various parameters may be adjusted to control the size of the droplets 40 as well as their formation rate. As noted herein, as the fluid passes the step 20, pinch off occurs passively to create the droplets 40 of a geometrically-determined size. The length of the terraced region 24 may be varied to adjust the size of the droplets 40. For example, larger sized droplets (e.g., 125 μm diameter) were found to be generated with a terrace region 24 having a length of 90 μm as compared to droplets (e.g., 85 μm diameter) for a terraced region 24 having a length of 60 μm. Even without the terraced region 24 droplets will, however, still form.

Figure 5C:
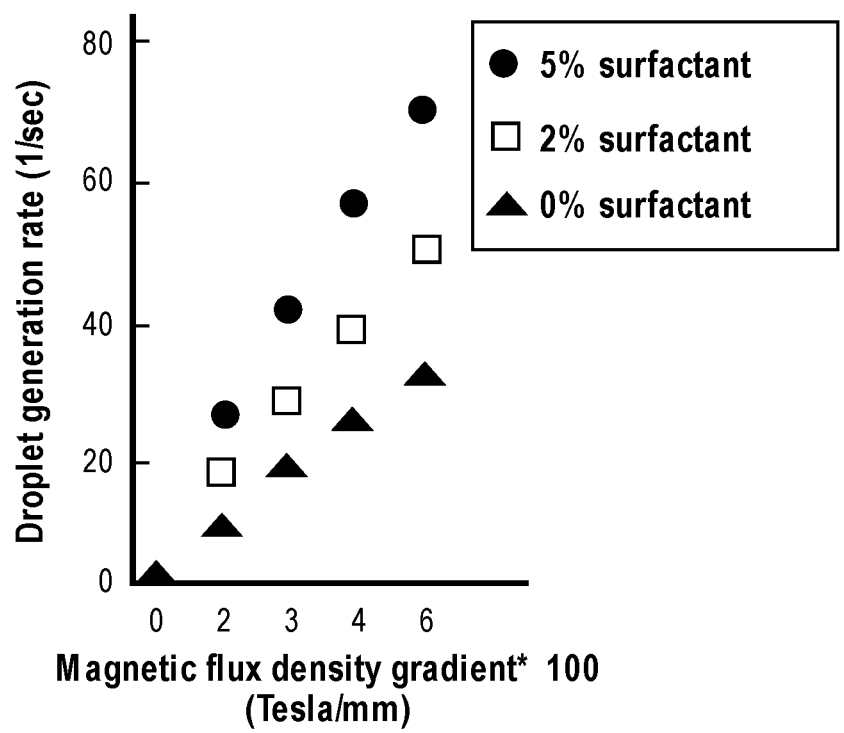
FIG. 5C illustrates a graph showing the droplet generation rate of the microfluidic device as a function of magnetic flux density gradient for differing amounts of surfactant (2% Pico-Surf™, 5% Pico-Surf™, and 0% surfactant (Novec™ 7500)).

Likewise, as explained herein, the rate of droplet generation may be increased by reducing the distance (D) between the moveable external magnet 30 and the step 20. Conversely, the droplet generation rate may be decreased by increasing the distance (D) between the moveable external magnet 30. In addition, it has been found that by increasing the surfactant concentration the droplet generation rate increases. Droplet generation thus increases as a function of increasing magnetic force and decreasing surface tension. By adjusting the position of the external magnet 30 to create a higher magnetic field gradient, droplet generation increases linearly with magnetic field gradient for both the Pico-Surf™/Novec™ 7500 continuous phase as well as the FC-40 continuous phase as seen by FIGS. 5A and 5B. In addition, increasing the surfactant (from 0% to 5% Pico-Surf™ in Novec™ 7500) reduces the surface tension force and droplet generation increases as seen in FIG. 5C. Note that in some embodiments, surfactant may not be needed or desired. For example, if the generated droplets 40 will be delivered to a subject as a therapeutic or medicament, one may not want the presence of the surfactant. Still other embodiments may require the presence of the surfactant to prevent coalescence of the droplets 40 post-formation. For example, for assays that are performed in individual droplets 40 and then imaged; the separation of droplets 40 is required. In such instances, surfactant may be present to prevent droplet coalescence.

Figure 8A:
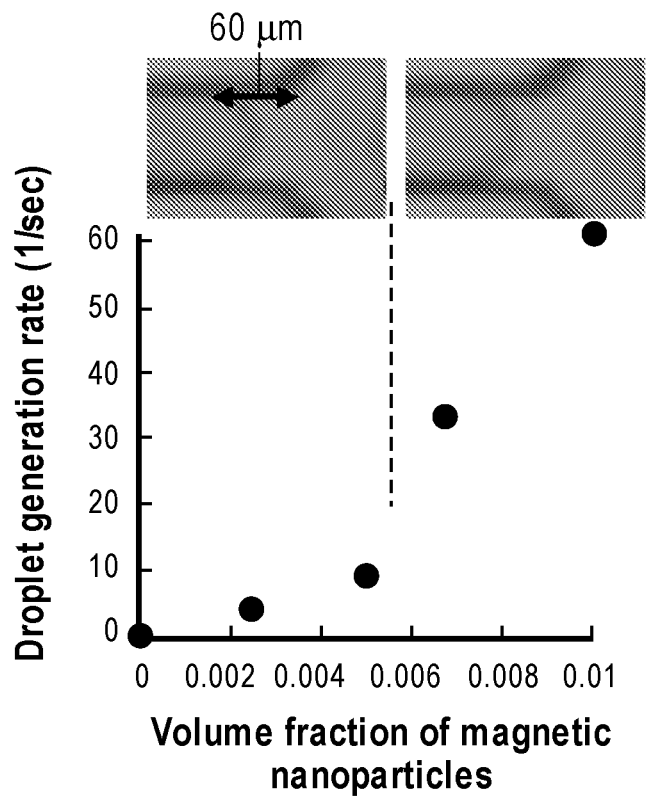
FIG. 8A illustrates a graph illustrating the droplet generation rate as a function of volume fraction of magnetic nanoparticles. Also illustrated in the graph are photographs of the step region of the microfluidic device showing nascent droplet generation. Below fractions of around 0.005 once the droplet is formed, fluid starts refilling just before the step with the leading meniscus being located proximal to the step around 60 µm. At fractions above 0.005 the ferrofluid starts refilling right at the step.

The driving force also increased with the addition of more magnetic nanoparticles 17 to the solution (e.g., increasing the volume fraction of magnetic nanoparticles 17) which resulted in a higher droplet generation rate as seen in FIG. 8A. The droplet generation rate increases by increasing the concentration of the magnetic nanoparticles 17. Even diluted ferrofluid 15 down to less than 10% of the initial stock solution can create droplets 40. The ability to create droplets 40 at lower ferrofluid 15 concentrations is important to be able to use the system for downstream assays. In this case, a sample volume, polymer precursor, or reagent volume can be mixed with the ferrofluid 15 in the ferrofluid reservoir 12 and still maintain the ability to create droplets 40 with more dilute mixed ferrofluid solution. When the continuous phase is Pico-Surf™, the droplet generation rate can be adjusted to be in a range between 0 to 12 droplets per second per microfluidic channel by changing the concentration of the magnetic nanoparticles 17 when the permanent magnet distance is fixed at a distance of 150 μm from the step 20. When FC-40 was used as the continuous phase the droplet generation rate is much lower compared to Pico-Surf™. Note that a parallelized version of the microfluidic device 10 such as that illustrated in FIG. 1C has much higher droplet generation rates due to parallel droplet formation (e.g., 100 droplets per second or higher).

Figure 8B:
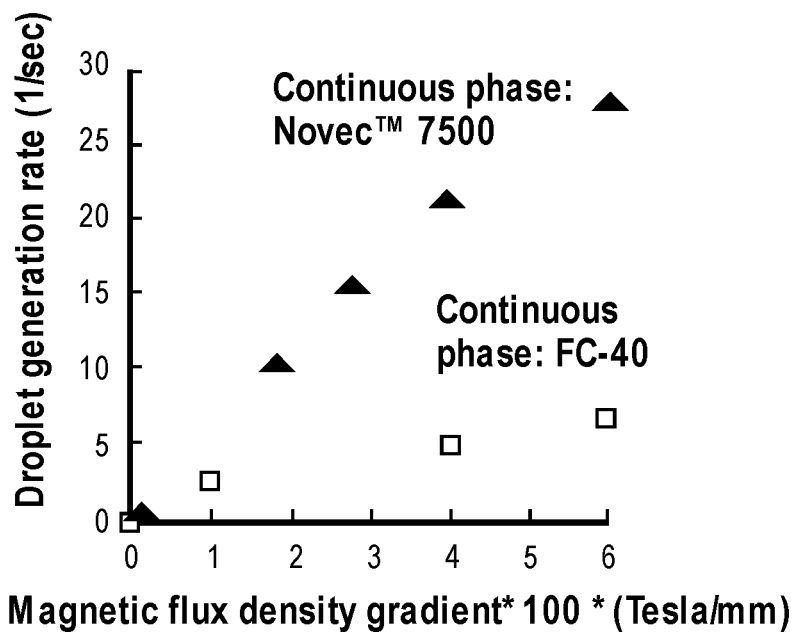
FIG. 8B illustrates a graph illustrating the droplet generation rate as a function of magnetic flux density for different viscosities of the continuous phase (e.g., Novec™ 7500 and FC-40).

The viscosity of the oil phase also plays a role in the rate of droplet formation. Decreasing the viscosity of the oil phase reduces fluidic resistance and droplet generation increases. With reference to FIG. 8B, by decreasing the viscosity (1.24 cP (Novec™ 7500) instead of 3.5 cP (FC-40)) fluidic resistance decreases and droplet generation increases (surface tension of Novec™ 7500 and FC-40 are 16.2 and 16 mN m$^{-1}$ respectively). The maximum droplet generation rate that was experimentally achieved with the cylindrical magnet (K&J Magnetics-D68) is about 80 droplets per second per connecting channel for 5 percent Pico-Surf™ oil using EMG 408 ferrofluid 15. Consequently, a 10 µl solution would be emulsified to 85 µm droplets in less than 10 (ten) minutes.

As explained herein, the a microfluidic device 10 such as that illustrated in FIG. 1D which has multiple ferrofluid reservoirs 12a, 12b, 12c may be used to mix reagents on-chip. One of the important features required for droplet or digital microfluidics is the ability to mix reagents on-chip and formal compartmentalized droplets afterwards. This is critical for some analytical approaches that rely on reactions because if the reactive reagents are mixed in a one-inlet device, reactions can initiate as soon as mixing occurs. Therefore, all droplets will contain products of the reaction such that concentration-dependent detection of the target present in each droplet is not possible, or reaction conditions are not controllable. FIG. 1D illustrates one embodiment that uses three ferrofluid reservoirs 12a, 12b, 12c although two or more such reservoirs 12 may be used. For example, in a two ferrofluid reservoir 12 embodiment, the moveable external magnet 30 may be positioned downstream of the step 10 (e.g., at a distance (D) of 50 µm) to have an equal magnetic body force on both solutions attracting them toward the droplet generating step 20 for uniform mixing. In the three ferrofluid reservoir embodiment of FIG. 1D, the three separate reagent are combined immediately upstream of step 20 where droplets 40 are generated. This enables reaction components to be quickly entrained in droplets 40. Note that while FIG. 1D illustrates the fluids contained in the respective ferrofluid reservoirs 12a, 12b, 12c being combined at a common junction it is possible two fluids are combined upstream prior to be being joined by the third or last ferrofluid 15 solution. Thus, mixing in a desired sequence of operations can be performed. In addition, various concentrations or different types of magnetic nanoparticles 17 can be used to adjust the relative amounts of the components that end up entrained in the droplets 40.

In another embodiment, a middle ferrofluid reservoir 12b contains no reagent, while two side reservoirs 12a, 12c contain reactive sample/reagent and no interaction is observed between the fluid present in the two side reservoirs while flowing through the connecting channel to the emulsification junction. Mixing is only initiated once a droplet 40 is formed. In a related embodiment, the different channels 14 extending from the different reservoirs 12a, 12b, 12c possess different fluidic resistance to control the relative flow rate of the fluids in each of the reservoirs that flow into the emulsification junction. One could also vary the amount of ferrofluid 15 with separate reagents in different ferrofluid reservoirs 12 and mix these reagents with controlled flow rates that depend on the ferrofluid 15 amount before droplet generation.

A wide variety of species, reagents, and cells can be used as part of the sample. Samples that could be introduced include diagnostic or research samples that include drugs, mammalian cells, bacteria, viruses, nucleic acids, protein biomarkers, microRNA, and/or exosomes. Samples or introduced fluids could also consist of polymer precursors. The reactions occurring in the droplets 40 could include nucleic acid amplification (e.g., polymerase chain reaction (PCR), loop-mediated isothermal amplification (LAMP), multiple displacement amplification (MDA), homogeneous entropy-driven biomolecular assay (HEBA), or other amplification strategies) followed by analysis of fluorescence using fluorophore-quencher probes or intercalating dyes. A digital nucleic acid amplification and readout could be conducted for example. This readout may be conducted following droplet generation in a reservoir or at some other downstream located chamber or region of the device 10 with or without having been pulled through the porous membrane 50. Alternatively, digital immunoassays could be performed in the droplets 40. In fact, any assay conducted in confined volumes using other methods of forming droplets 40, could be performed in this system. Alternatively, an amplified immunoassay could be performed in the droplets 40 using a fluorescent or colorimetric readout targeting a molecule in solution (e.g., cytokine from an activated or resting leukocyte or antibody produced by a B cell or hybridoma) or attached to a bioparticle in the sample (e.g., cell, virus, bacterium).

Alternatively, analysis of secretions from cells could be performed using an immunoassay or fluorogenic substrates for enzymes (e.g., substrates for proteases, caspases, or esterases), using the confined volume of the droplet 40 to concentrate secretions for readout. To enhance detection, magnetic droplets 40 could be brought to a desired surface or location using magnetic control, or magnetic nanoparticles 17 in the droplets 40 could be pulled to the side or bottom of a droplet 40 to prevent interference with biochemical assays or imaging. The droplets 40 may also be pulled through a porous membrane 50 as described herein and exposed to a suspension of cells contained on the top or opposing side of the porous membrane 50. Magnetic droplets 40 could also be brought to a reservoir surface using a magnetic field to initiate a reaction with a surface-bound reagent. Another reaction would include single-cell whole genome amplification within each droplet 40 with or without barcoded magnetic nanoparticles 17 (e.g., according to the Dropseq protocol). Another approach is to perform whole genome amplification across many droplets from a sample to reduce bias in amplification (e.g., see Yanyi Huang PNAS 2015).

Readout of the assays could be done with a variety of techniques, e.g., using a lens-based microscopic system that images a downstream droplet reservoir or the like to perform quantification. Alternatively, lens-free imaging systems described by Ozcan et al. (e.g., Digital Readout Platform for Water-In-Oil Droplet Immunoassays Running on a Cell-Phone for Point of Care Viral Load Sensing, MicroTAS 2012; The 16th International Conference on Miniaturized Systems for Chemistry and Life Sciences, Okinawa, Japan (Oct. 28-Nov. 1, 2012), using over-the-counter readers/imagers such as mobile phones, digital cameras, or flatbed scanners. In the embodiment where droplets 40 are guided to an outlet channel in single file a flow cytometry type reader setup consisting of a filtered excitation and emission collected by a PMT or photodiode is possible.

In some embodiments that utilize a porous membrane 50, there is no need for a magnet 36 that is used to pull the droplets 40 through a porous membrane 50. For example, if the porous membrane 50 has pore sizes that are large (e.g., larger than diameter of the droplet 40) and the droplets 40 experience a buoyant force within the continuous phase, the droplets 40 may naturally rise and pass through the porous membrane 50. This process can be aided by choosing a high density continuous phase (e.g., like Pico-Surf™). If there are particles or other species contained within the droplets 40, this method could be used to separate droplets 40 based on different densities and sizes (e.g., different numbers of encapsulated particles or species).

The porous membrane based embodiment of FIGS. 6A and 6B could also be used as a microfluidic magnetometer for fluids. If the release rate of droplets 40 through the porous membrane 50 is calibrated having a magnet 36 with a known magnetic strength and a fluid with a known magnetic susceptibility, then one can use the observed release rate of droplets 40 in a fluid with unknown magnetic properties to calculate or determine its magnetic susceptibility.

In still another application of the porous membrane based embodiment of FIGS. 6A and 6B, plasma may be purified from blood for low volume processing. After blood is mixed with magnetic nanoparticles 17, droplets 40 are generated by applying a magnetic field and then the droplets 40 are attracted toward the porous membrane 50 by moving the magnet 30, 36 and components smaller than the pore size of the porous membrane 50 will squeeze or pass through the porous membrane 50 and larger components remain in the microfluidic device 10.

Still another application of the porous membrane based embodiment of FIGS. 6A and 6B is in applications or experiments where access to oxygen is needed. For example, cells may be encapsulated in droplets 40 and brought adjacent to the porous membrane 50 that is exposed on one side to air to provide access to oxygen. Oxygen may be exchanged with the cells through the small volume of liquid contained in the droplets 40.

This technique should impact the variety of applications in which microfluidic confinement or droplet generation is used for assays (especially digital assays) or fabrication. One main application would be using this device for digital assays at a point-of-care, where one could easily manipulate samples (mix, emulsify and move) and reagents in the form of discrete droplets (Digital PCR, etc.). In this case, no bulky pumps or complex footprint would be needed for the instrument. This could bring digital assays to point-of-care diagnostics instead of analog PCR or other nucleic acid tests for example for pathogen nucleic acid analysis. Digital assays have some advantages in terms of quantification compared to analog assays. In addition analysis is possible from a small volume given the small dead volume of our system compared to pump-based systems. The complexity of multiple assay steps/reagents is also reduced when pulling magnetic fluid from separate reservoirs instead of pushing fluids together using pumping.

Another application is that the microfluidic device 10 can be used as a controlled mechanism for time-sensitive reactions, where reagents should only be mixed at a certain time by having two or more separate reservoirs containing different reagents mixed with ferrofluid having different concentrations of magnetic nanoparticles 17. Thus, different reservoirs may be loaded with ferrofluids 15 with varying concentrations of magnetic nanoparticles 17. Ferrofluid reservoirs 12 may also be located at different locations on the microfluidic device 10 such that they experience differential forces from the magnet 30. These options could be used to mix different amount of each reagent in the droplet 40.

As explained herein, it is also possible that two reagents merge and then downstream the third reagent mixes with those two. This gives extra time for the first two reagents to start a specific reaction and then the third one could be added at the desired time before the step emulsification region. This can be controlled by designing the order or sequence of junctions of the various microfluidic channels 14 prior to the step region 18. In this case one or more permanent magnets could be used. The fluorescent readout could be one way of analyzing this type of experiment. One can also adjust the flow rate of each reagent by adding different concentration of magnetic nanoparticles 17 to the different ferrofluid reservoirs 12.

Another application could be making different types of magnetic polymer or hydrogel particles (even for example Janus particles) if UV is applied right after droplet generation to polymerize the droplets 40, or a reaction requiring two components is initiated upon mixing two streams. In such an embodiment, the ferrofluid would likely be an organic-based fluid while the continuous phase would be aqueous-based.

Another application of the device and method is active sorting of cells and particles encapsulated in droplets 40 containing ferrofluid 15. For example, when the droplet 40 is forming at the step region 18, the encapsulated particle is detected (either by the size measurement or fluorescence signal of the labeled particles) then the magnet 30 (or a different magnet) could move to the top part of the continuous phase reservoir 16 to collect those droplets 40 there; and when the droplet 40 is empty or smaller particles are detected the magnet 30 moves to the bottom of the reservoir to collect these type of droplets in a separate location.

In addition, if the continuous-phase reservoir 16 is long enough one can measure the velocity of the formed droplets 40 and depending on the content of the droplet 40 (e.g., the amount of magnetic nanoparticles 17, particles or cells inside droplet, etc.) the droplets 40 will move with different velocities toward the magnet 30. This could also be used as a metric for analyzing how pure a sample is or collecting only a fraction of droplets 40 with particular reagents.

While embodiments of the present invention have been shown and described, various modifications may be made without departing from the scope of the present invention. For example, features or aspects of one embodiment may be incorporated in other embodiments even if not specifically identified as being substitutable. The invention, therefore, should not be limited, except to the following claims, and their equivalents.

What is claimed is:

1. A method of forming droplets in a microfluidic device using a ferrofluid comprising:
   providing a microfluidic device having one or more ferrofluid reservoirs containing a ferrofluid therein and a continuous-phase reservoir containing an oil therein, wherein the one or more ferrofluid reservoirs are coupled to the continuous-phase reservoir via one or more microfluidic channels, the continuous-phase reservoir comprising a step region having an increased height as compared to a height of the one or more microfluidic channels; and
   applying an external magnetic field to the microfluidic device, wherein the external magnetic field moves the ferrofluid solution along the one or more microfluidic channels and generates droplets in the continuous-phase reservoir.

2. The method of claim 1, wherein the one or more microfluidic channels interface with the step region at a terraced region, the terraced region having a height equivalent to the height of the one or more microfluidic channels.

3. The method of claim 1, wherein a plurality of microfluidic channels connect between a single ferrofluid reservoir and the continuous-phase reservoir.

4. The method of claim 1, wherein the ferrofluid comprises an aqueous solution containing magnetic nanoparticles suspended therein.

5. The method of claim 4, wherein the magnetic nanoparticles have a diameter that is less than 100 nm.

6. The method of claim 1, wherein the ferrofluid solution comprises a mixture of a sample solution and an aqueous ferrofluid solution.

7. The method of claim 6, wherein the sample solution comprises one or more reagents.

8. The method of claim 6, wherein the sample solution comprises one or more cells.

9. The method of claim 1, further comprising imaging the droplets.

10. The method of claim 1, further comprising passing at least some of the droplets through a porous membrane located in the continuous-phase reservoir by applying an external magnetic field to the droplets.

11. The method of claim 1, wherein the microfluidic device has a plurality of ferrofluid reservoirs, each containing a different reagent and a ferrofluid.

12. The method of claim 11, wherein the plurality of ferrofluid reservoirs contain differing concentrations of magnetic nanoparticles.

13. A method of forming droplets in a microfluidic device using a ferrofluid comprising:
providing a microfluidic device having one or more ferrofluid reservoirs containing an organic ferrofluid therein and a continuous-phase reservoir containing an aqueous solution therein, wherein the one or more ferrofluid reservoirs are coupled to the continuous-phase reservoir via one or more microfluidic channels, the continuous-phase reservoir comprising a step region having an increased height as compared to a height of the one or more microfluidic channels; and
applying an external magnetic field to the microfluidic device, wherein the external magnetic field moves the organic ferrofluid solution along the one or more microfluidic channels and generates organic droplets in the continuous-phase reservoir.

14. The method of claim 13, further comprising passing at least some of the droplets through a porous membrane located in the continuous-phase reservoir by applying an external magnetic field to the droplets.

15. A microfluidic device for forming droplets comprising:
at least one ferrofluid reservoir disposed in the microfluidic device and containing a ferrofluid therein;
a continuous-phase reservoir disposed in the microfluidic device and containing an oil phase therein;
one or more microfluidic channels connecting between the at least one ferrofluid reservoir and the continuous-phase reservoir, the continuous-phase reservoir comprising a step region having an increased height as compared to a height of the one or more microfluidic channels; and
a moveable external magnet located adjacent to the microfluidic device.

16. The microfluidic device of claim 15, wherein the one or more microfluidic channels interface with the step region at a terraced region, the terraced region having a height equivalent to the height of the one or more microfluidic channels.

17. The microfluidic device of claim 15, wherein a plurality of microfluidic channels connect between one of the at least one ferrofluid reservoir and the continuous-phase reservoir.

18. The microfluidic device of claim 15, further comprising a track or stage for moving the external magnet.

19. The microfluidic device of claim 15, wherein the continuous-phase reservoir comprises a porous membrane disposed therein, and further a secondary liquid phase disposed on a side of the porous membrane opposite a side contained in the continuous-phase reservoir.

20. The microfluidic device of claim 19, further comprising a collection chamber disposed on a side of the porous membrane opposite a side contained in the continuous-phase reservoir.

* * * * *